(12) United States Patent
Barbato

(10) Patent No.: US 7,058,211 B2
(45) Date of Patent: Jun. 6, 2006

(54) ELECTRONICS INTERFACE FOR AN ULTRASOUND CONSOLE

(75) Inventor: Louis J. Barbato, Franklin, MA (US)

(73) Assignee: Scimed Life Systems, Inc., Maple Groce, MN (US)

( * ) Notice: Subject to any disclaimer, the term of this patent is extended or adjusted under 35 U.S.C. 154(b) by 802 days.

(21) Appl. No.: 09/909,357

(22) Filed: Jul. 18, 2001

(65) Prior Publication Data

US 2003/0137670 A1    Jul. 24, 2003

(51) Int. Cl.
G06K 9/00 (2006.01)
(52) U.S. Cl. .................................. 382/128; 600/447
(58) Field of Classification Search ............ 382/128; 713/618, 620; 424/9.51; 600/447, 437, 600/457, 443, 459; 73/620
See application file for complete search history.

(56) References Cited

U.S. PATENT DOCUMENTS

| | | | |
|---|---|---|---|
| 5,465,147 A * | 11/1995 | Swanson | 356/497 |
| 5,523,788 A * | 6/1996 | Kannegundla et al. | 348/321 |
| 5,538,004 A | 7/1996 | Bamber | 128/662.06 |
| 5,588,434 A * | 12/1996 | Fujimoto | 600/443 |
| 5,692,507 A * | 12/1997 | Seppi et al. | 600/407 |
| 5,830,145 A | 11/1998 | Tenhoff | 600/463 |
| 5,943,133 A | 8/1999 | Zeylikovich et al. | 356/496 |
| 5,949,929 A | 9/1999 | Hamm | 385/25 |
| 6,134,003 A | 10/2000 | Tearney et al. | 356/477 |
| 6,363,033 B1 * | 3/2002 | Cole et al. | 367/138 |
| 6,390,978 B1 | 5/2002 | Irion et al. | 600/437 |

FOREIGN PATENT DOCUMENTS

EP    1 090 582 A1    11/2001

OTHER PUBLICATIONS

LightLab Imaging, LLC, "Advantages of OTC" and "What is OCT?" *LightLab* ™ *Optical Coherence Tomography*, http://www.lightlabimaging.com/, © 2000, 3 pp.

(Continued)

*Primary Examiner*—Sheela Chawan
(74) *Attorney, Agent, or Firm*—Orrick Herrington & Sutcliffe LLP

(57) ABSTRACT

Systems and methods for interfacing an Optical Coherence Domain Reflectometry (OCDR) system to an ultrasound console are provided. A first electronics interface embodiment processes parallel channel outputs of the OCDR system into a serial analog signal for input to an ultrasound console. Another electronics interface embodiment processes the parallel channel outputs of the OCDR system into a digital data sequence for input to an ultrasound console having a digital input. Yet another electronics interface embodiment processes a multiplexed output from a multiplexed photo array into an analog or digital form for input to an ultrasound console. Still another electronics interface embodiment processes a plurality of multiplexed outputs from a multiplexed photo array into an analog or digital form for input to an ultrasound console.

17 Claims, 4 Drawing Sheets

OTHER PUBLICATIONS

Zeylikovich, I. et al., "Nonmechanical grating-generated scanning coherence microscopy," *Opyics Letters*, vol. 23, No. 23, Dec. 1, 1998, pp. 1797-1799.

"Optical Coherence Tomography: Principles, Instrumentation and Applications," Abstract only, presented at IREE Society XXIst Australian Conference on Optical Fibre Technology, Dec. 1996, Brisbane, Australia, 4 pp.

Jiang, Yuan, "IV.12—Avalance Photodiodes (APD's)?" *The Unusual Diode FAQ*, Avtech Electrosystems Ltd., http://www.avtechpulse.com/faq.html/IV.12/, undated, 3 pp.

Pitris, C. et al., "High Resolution Imaging of Neoplastic Changes in Gynecological Tissue Usint Optical CoherenceTomography," Abstract only, *American Society of Clinical Oncology*, © 1998, http://www.asco.org/prof/me/html/98abstracts/gync/m_1434.htm.

Kuz'minov, Yu S., *Lithium Niobate Crystals*, Abstract and Contents only, May 1999, 180 pp., http://www.demon.co.uk/cambsci/book10.htm.

* cited by examiner

ELECTRONICS INTERFACE FOR AN ULTRASOUND CONSOLE

FIELD OF THE INVENTION

The invention relates generally to an electronic interface to an ultrasound console, and more particularly to an electronics interface for interfacing an Optical Coherence Domain Reflectometry (OCDR) system to an ultrasound console.

BACKGROUND OF THE INVENTION

Ultrasound medical imaging is often used to produce images of blood vessels and surrounding tissue. To image a blood vessel and surrounding tissue, an Intravascular Ultrasound (IVUS) catheter is typically used. The IVUS catheter comprises an elongated member and an ultrasound transducer located at a distal end of the elongated member. The elongated member is inserted into the blood vessel, and the ultrasound transducer is positioned at a desired location in the blood vessel. An ultrasound transducer is designed to transmit a specific resonant frequency, e.g., when it is excited by a pulse. The excite pulse signal causes the ultrasound transducer to emit ultrasound waves in the blood vessel. A portion of the emitted ultrasound waves is reflected back to the ultrasound transducer at tissue boundaries in the blood vessel and the surround tissue. The reflected ultrasound waves induce an echo signal at the ultrasound transducer. The echo signal is transmitted from the ultrasound transducer to an ultrasound console, which typically includes an ultrasound image processor and a display. The ultrasound console uses the received echo signal to image the blood vessel and the surrounding tissue.

In order to produce a radial cross-sectional image of a blood vessel and surrounding tissue, the ultrasound transducer is typically rotated along the axis of the elongated member. As the ultrasound transducer is rotated, the ultrasound transducer emits ultrasound waves in different radial directions. The resulting echo signals from the different radial directions are processed by the ultrasound console to produce a radial cross-sectional image of the blood vessel and the surrounding tissue. Alternatively, the ultrasonic transducer may be mounted in an assembly together with a reflective member (mirror), where the transducer emits ultrasonic energy in a substantially axial direction and the mirror is oriented to deflect the emitted ultrasonic energy in a radial direction.

The echo signal is a serial amplitude modulated signal, in which the amplitude of the signal varies with time. A typical echo signal has a time length of 8 μs, which corresponds to an image depth of approximately 6 millimeters from the ultrasound transducer. The echo signal carries both image brightness information and image depth information, where depth may be taken with respect to the ultrasound transducer. The image brightness information is provided by the amplitude of the echo signal. The image depth information is provided by the time position within the echo signal. For example, an earlier time position in the echo signal corresponds to a lower image depth than a later time position in the echo signal. This is because an ultrasound wave that is reflected back to the ultrasound transducer from a shallower depth reaches the ultrasound transducer before an ultrasound wave that is reflected back to the ultrasound transducer from a deeper depth. As a result, the ultrasound wave that is reflected back to the ultrasound transducer from the shallower depth has a shorter propagation delay time, which translates into an earlier time position in the echo signal.

Another imaging technique used to produce images of blood vessels and surrounding tissue is Optical Coherence Domain Reflectometry (OCDR). To image a blood vessel using OCDR, a fiber-optic catheter is inserted into the blood vessel. A proximal end of the fiber-optic catheter is coupled to an OCDR system. In the OCDR system, a laser generates a source beam. A beam splitter splits the source beam into a reference beam and a sample beam. The reference beam is diffracted by a diffraction grating into a diffraction beam. The sample beam is transmitted through the fiber-optic catheter and emitted in the blood vessel at a distal end of the catheter. Typically, the distal end of the catheter includes a prism for directing the sample beam into the blood vessel. A portion of the sample beam is reflected back to the distal end of the catheter by the blood vessel and the surrounding tissue. The reflected sample beam is transmitted to the OCDR system through the fiber-optic catheter. In the OCDR system, the reflected beam is mixed with the diffraction beam to produce a coherence-domain interference pattern, which is detected by an array of photo detectors.

The resulting interference pattern provides both image brightness information and image depth information, where depth may be taken with respect to the distal end of the catheter. The image brightness information is provided by the light intensity of the interference pattern. The image depth information is provided by the spatial position within the interference pattern. This is because the portion of the sample beam that is reflected back to the catheter from a certain depth in the body constructively interferes with the diffraction beam at a certain spatial position. Typically, the photo detectors of the photo array are arranged so that each photo detector detects the light intensity of the interference pattern at a certain spatial position within the interference pattern. Thus, the output of each photo detector provides image brightness information for a certain image depth. The photo array outputs parallel channels, where each parallel channel corresponds to the output of one of its photo detectors. The parallel channels of the photo array are inputted to an OCDR image processor to produce an image of the blood vessel and the surrounding tissue.

An advantage of the above-described OCDR system is that the array of photo detectors is able to capture image brightness information at multiple image depths in one instance. This enables the OCDR system to produce images at true video rates, e.g., 30 frames per second.

It would be desirable to provide an electronics interface that processes the parallel channel outputs of the photo array of the OCDR system into a serial amplitude modulated signal that can be processed by an ultrasound console. Such an electronics interface would enable the same ultrasound console to process and display both ultrasound images and OCDR images, thereby reducing costs.

SUMMARY OF THE INVENTION

The invention relates to systems and methods for interfacing an OCDR system with an ultrasound console.

In one example embodiment of a system built in accordance with the invention, an electronics interface is coupled between the parallel channel outputs of a photo array of an OCDR system and an ultrasound console. The electronics interface includes a plurality of channel processors, where each channel processor is coupled to one of the parallel channel outputs of the photo array. Each channel processor preferably further includes an analog processor, an A/D converter, a First-In-First-Out (FIFO) memory buffer, and a data bus coupled to the FIFO memory buffer of each one of the channel processors. The electronics interface further may include a single FIFO memory buffer coupled to the data bus and a D/A converter coupled to the output of the single FIFO memory buffer. The output of the D/A converter is coupled to the input of the ultrasound console. The electronics interface further may include a controller coupled to an ultrasound motor encoder. The controller uses encoder pulses outputted by the motor encoder to synchronize the operation of the electronics interface with the ultrasound console.

During operation, each one of the parallel channel outputs of the photo array outputs a signal carrying image brightness information for a certain image depth. Each channel processor of the electronics interface processes one of the parallel channel outputs of the photo array. The analog processor of each one of the channel processors performs analog processing on the respective parallel channel output such as signal amplification, bandpass filtering, and/or logarithmic amplification. The output of each analog processor is coupled to the respective A/D converter.

When the controller receives a first encoder pulse from the motor encoder, the controller instructs each one of the A/D converters to digitize the analog output from the respective analog processor for a predetermined data acquisition time. During this time, each A/D converter writes its digital data into the respective FIFO memory buffer. At the end of the data acquisition time, the FIFO memory buffers of the channel processors sequentially write their digital data into the single FIFO memory buffer via the data bus.

When the controller receives a second (subsequent) encoder pulse from the motor encoder, the controller instructs the single FIFO memory to output its stored digital data to the D/A converter. Preferably, the single FIFO memory buffer outputs its digital data to the D/A converter in the form of a serial digital data sequence in which the digital data in the digital data sequence are arranged in order of increasing image depth. The D/A converter converts the serial digital data sequence from the single FIFO memory buffer into a serial analog signal, which is outputted to the ultrasound console.

In another embodiment, the electronics interface is coupled between the parallel channel outputs of the photo array of the OCDR system and a digital input of an ultrasound console. In this embodiment, the serial digital data sequence from the single FIFO memory buffer is outputted to the digital input of the ultrasound transducer.

In yet another embodiment, the electronics interface is coupled between a multiplexed photo array and an ultrasound console. During operation, the multiplexed photo array outputs two channels to the electronics interface. Each one of the two channels sequentially outputs signals from half of the photo detectors of the multiplexed photo array to the electronics interface. The electronics interface processes the two channels of the multiplexed photo array into a serial analog signal or a digital data sequence for input to an ultrasound console.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 1:
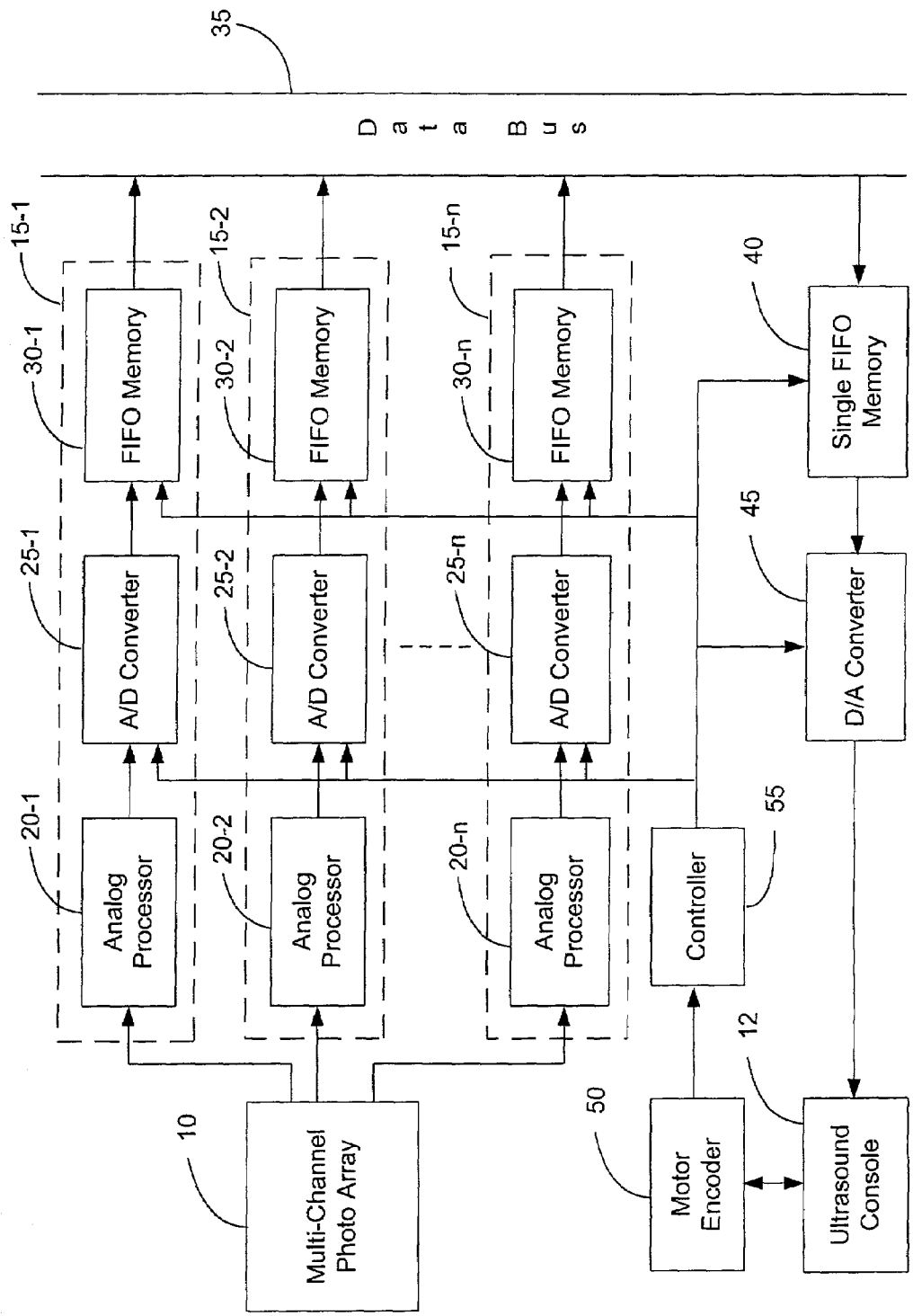
FIG. 1 is a block diagram illustrating an example embodiment of an electronics interface.

FIG. 1 shows an example embodiment of an electronics interface between an OCDR system and an ultrasound console. The electronics interface system is coupled between a multi-channel photo array 10 of an OCDR system and an ultrasound console 12. The photo array 10 comprises a plurality of photo detectors (not shown), e.g., 256 photo detectors. Each photo detector of the photo array 10 outputs a signal carrying image brightness information for a certain image depth. The photo detectors may be photodiodes, Charge Coupled Devices (CCDs), or the like. The photo array outputs a plurality of parallel channels, where each one of the parallel channels corresponds to the output of one of its photo detectors.

The electronics interface includes a plurality of channel processors 15-1 to 15-n, where each channel processor 15-1 to 15-n is coupled to one of the parallel channel outputs of the photo array 10. Each channel processor 15-n includes an analog processor 20-n, an A/D converter 25-n, and a First-In-First-Out (FIFO) memory buffer 30-n. For the sake of simplicity, the reference numeral 15-n refers to any of the channel processors 15-1 to 15-n; 20-n refers to any of analog processors 20-1 to 20-n; 30-n refers to any of FIFO memory buffers 30-1 to 30-n. The electronics interface also includes a data bus 35 coupled to the output of each one of the FIFO memory buffers 30-n of the channel processors 15-n. The electronics interface further includes a single FIFO memory buffer 40 coupled to the data bus 35, a digital-to-analog (D/A) converter 45 coupled to the output of the single FIFO memory buffer 40, and a controller 55. The output of the D/A converter 45 is coupled to the input of the ultrasound console 12. The controller 55 is also coupled to the analog-to-digital (A/D) converters 25-1 to 25-n, the FIFO memory buffers 30-1 to 30-n, the single FIFO memory 40 buffer, and the D/A converter 45. The ultrasound console 12 and the controller 55 are each coupled to an ultrasound motor encoder 50 of an ultrasound Patient Interface Unit (PIU). The ultrasound motor 50 outputs encoder pulses which may be spaced, for example, 130 µs apart, to the ultrasound console 12 and the controller 55. The controller 55 uses the received encoder pulses to synchronize the operation of the electronics interface with the ultrasound console 12.

During operation, each photo detector of the photo array 10 outputs a signal, such as a current, to one of the parallel channel outputs of the photo array 10. The signal of each one of the parallel channel outputs may carry image brightness information for a certain image depth, where depth may be taken with respect to a catheter. Each channel processor 15-n of the electronics interface processes one of the parallel channel outputs of the photo array 10. The analog processor 20-n of each channel processor 15-n performs analog processing on the respective parallel channel output signal. The analog processing may include current-to-voltage conversion, signal amplification, bandpass filtering, logarithmic amplification and/or other functions. Logarithmic amplification may be used to translate the signal in the channel processor 15-n to a log scale in order to increase the dynamic range of the signal, for example, to a dynamic range of 100 dB. The output of each analog processor 20-n is coupled to the respective A/D converter 25-n.

When the controller 55 receives a first encoder pulse from the motor encoder 50, the controller 55 instructs each A/D converter 25-n to digitize the analog output from the respective analog processor 20-n for a predetermined data acquisition time, such as 100 μs. During this time, each A/D converter 25-n writes its digital data into the respective FIFO memory buffer 30-n. At the end of the data acquisition time, the controller 55 instructs the FIFO memory buffers 30-1 to 30-n of the channel processors 15-1 to 15-n to sequentially write their digital data into the single FIFO 40 via the data bus 35. Preferably, the controller 55 instructs the FIFO memory buffers 30-1 to 30-n of the channel processors 15-1 to 15-n corresponding to lower image depths to write their digital data into the single FIFO memory buffer 40 before the FIFO memory buffers 30-1 to 30-n of the channel processors 15-1 to 15-n corresponding to deeper image depths. That way, the digital data from the channel processors 15-1 to 15-n are written into the single FIFO memory buffer 40 in order of increasing image depth.

When the controller 55 receives a second (subsequent) encoder pulse from the motor encoder 50, the controller 55 instructs the single FIFO memory 40 to output its stored digital data, which was taken during the previous encoder pulse, to the D/A converter 45. Preferably, the single FIFO memory buffer 40 outputs the digital data to the D/A converter 40 in the form of a serial digital data sequence in which the digital data in the digital data sequence are arranged in order of increasing image depth. The D/A converter 45 converts the digital data sequence from the single FIFO memory buffer 40 into a serial analog signal, which is outputted to the input of the ultrasound console 12.

Also, during the second encoder pulse, the controller 50 instructs each one of the A/D converters 25-n of the channel processors 15-n to acquire a new set of digital data, which is outputted to the ultrasound console 12 in serial analog form during a third encoder pulse. For each encoder pulse, the electronics interface outputs a serial analog signal to the ultrasound console 12 containing image data that was acquired during a previous encoder pulse. Thus, the electronics interface lags behind the ultrasound console by one encoder pulse, typically 130 μs.

The serial analog signal outputted by the D/A converter 45 may carry both image brightness information and image depth information. The image brightness information is provided by the amplitude of the serial analog signal. The image depth information is provided by the time position within the serial analog signal. An earlier time position in the serial analog signal corresponds to a lower image depth than a later time position in the serial analog signal. This is because the serial analog signal was converted from a serial digital data sequence whose digital data were arranged in order of increasing image depth.

The D/A conversion rate of the D/A converter 40 may be adjusted so that the serial analog signal has approximately the same time length as a typical echo signal, such as 8 μs. In addition, a mixer (not shown), which may be a Double Side-Band Suppressed Carrier (DSBSC) mixer or other kinds of mixers, may be used to adjust, i.e., translate, the frequency of the serial analog signal before it is inputted to the ultrasound console 12. For example, the mixer may be used to adjust the frequency of the serial analog signal to the frequency of a typical echo signal that the ultrasound console 12 is configured to receive.

Therefore, the electronics interface processes the parallel channel outputs of the photo array 10 of the OCDR system into a serial analog signal. The serial analog signal is similar to the echo signal of an ultrasound transducer in that it carries image brightness information and image depth information in a similar manner to a typical echo signal. This enables the ultrasound console 12 to process the serial analog signal outputted by the electronics interface into an image. In addition, the time length and/or frequency of the serial analog signal may be adjusted to better match the time length and/or frequency of a typical echo signal that the ultrasound console 12 is configured to receive.

Figure 2:
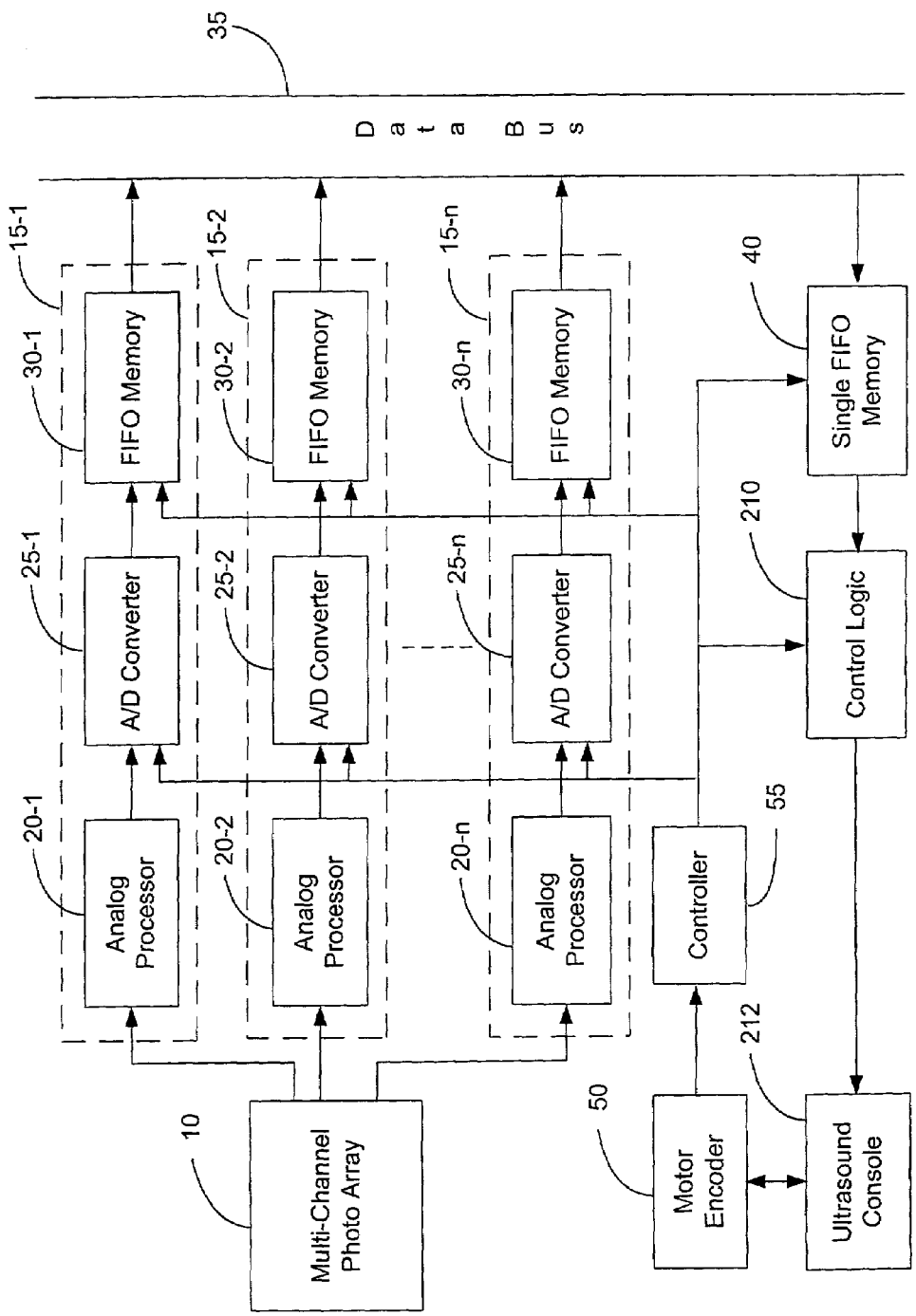
FIG. 2 is a block diagram illustrating another example embodiment of an electronics interface.

FIG. 2 shows an electronics interface according to another example embodiment of the electronics interface. The electronics interface according to this embodiment is coupled between the multi-channel photo array 10 of an OCDR system and an ultrasound console 212 having a digital input. The digital input enables the ultrasound console 212 to receive echo signals that have been digitized by a D/A converter. The digital input of the ultrasound console 212 may use, for example, a Versa Module Eurocard (VME) bus and/or a Peripheral Component Interconnect (PCI) bus to receive digital data.

The electronics interface according to this embodiment includes a control logic 210 in place of the D/A converter 45. The D/A converter 45 is not needed because the ultrasound console 212 has a digital input. The control logic 210 is coupled to the output of the single FIFO memory buffer 40 and the digital input of the ultrasound console 212.

The control logic 210 controls the transfer of the digital data sequence from the single FIFO memory buffer 40 to the digital input of the ultrasound console 212. Preferably, the control logic 210 transfers one digital data sequence for each encoder pulse of the motor encoder 50. For the case in which the digital input of the ultrasound console 212 uses a PCI bus, the control logic 210 may also perform handshaking functions to coordinate the transfer of data from the single FIFO memory buffer 40 to the digital input of the ultrasound console 212.

The ultrasound console 212 according to this embodiment may also include a software-based module for interpreting the digital data sequence received from the electronics interface. For example, the digital data in the digital data sequence may be arranged in order of increasing image depth so that the different data positions in the digital data sequence correspond to different image depths. In this example, the software-based module may translate the different data positions in a received digital data sequence into their corresponding image depths. The digital data and their corresponding image depths may then be inputted to the ultrasound image processor of the ultrasound console 212 to produce an image.

Figure 3:
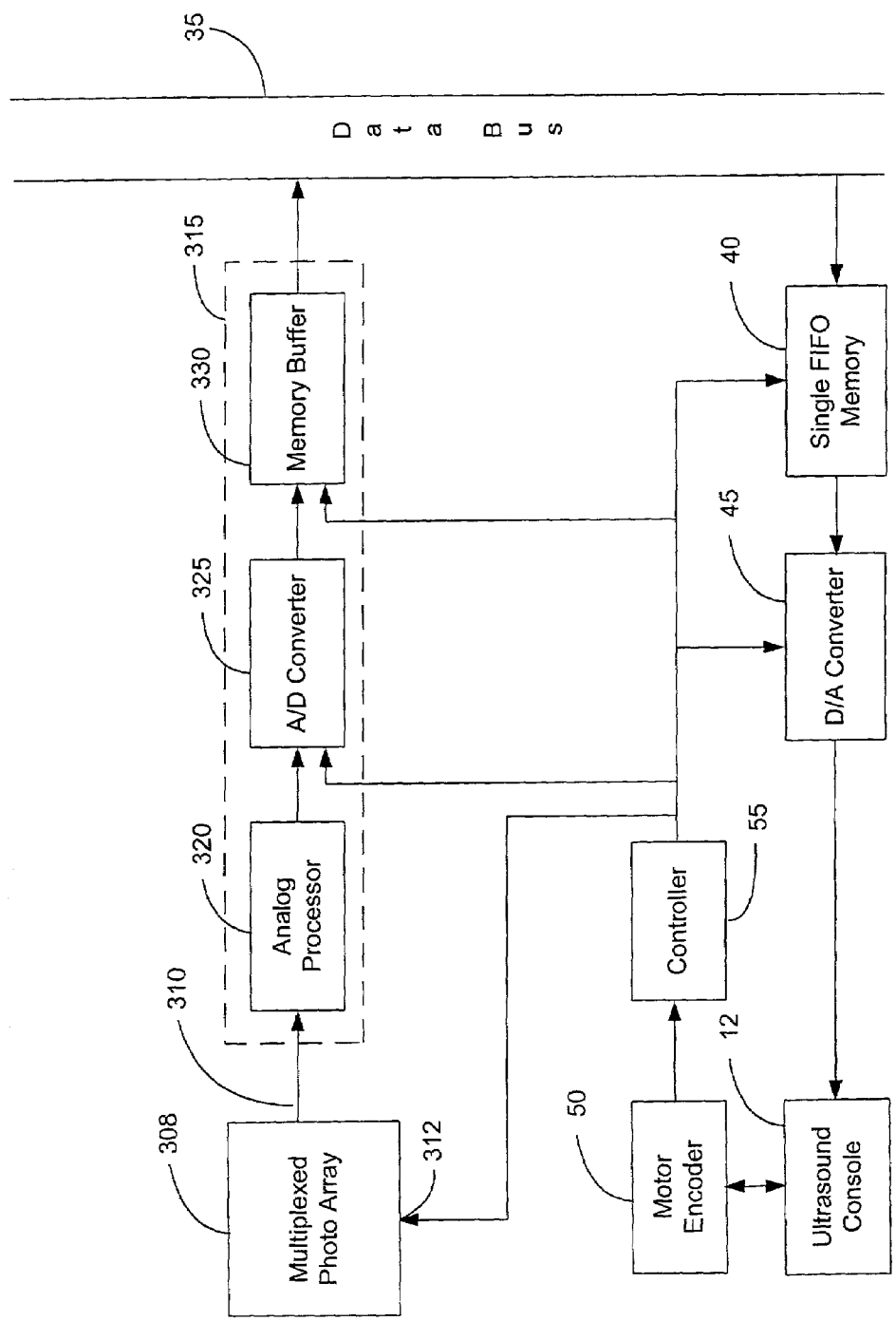
FIG. 3 is a block diagram illustrating an electronics interface coupled between a single-channel multiplexed photo array and an ultrasound console.

FIG. 3 illustrates yet another embodiment of the electronics interface. The electronics interface according to this embodiment is coupled between a multiplexed photo array 308 of an OCDR system and an ultrasound console 12. The multiplexed photo array 308 comprises a plurality of photo detectors (not shown), such as 256 photo detectors. Each photo detector of the multiplexed photo array 308 outputs a signal carrying image brightness information for a certain depth. The multiplexed photo array 308 according to this embodiment further includes a channel output 310 and a control input 312. The output of each one of the photo detectors of the multiplexed photo array 308 can be dynamically coupled to the channel output 310 via a switching network (not shown). The switching network is configured to couple the output of one of the photo detectors to the channel output 310 at a certain time and is controlled by the control input 312.

The electronics interface includes a channel processor 315 coupled to the channel output 310 of the multiplexed photo array 308. The channel processor 315 includes an analog processor 320 and an A/D converter 325. The electronics interface also includes a memory buffer 330, such as a RAM memory or any other kind of memory, coupled to the output of the A/D converter 325. The output of the memory buffer 330 is coupled to the data bus 35 of the electronics interface. The controller 55 of the electronics interface is coupled to the control input 312 of the multiplexed photo array 308. The controller 55 is also coupled to the A/D converter 325, memory buffer 330, D/A converter 45, the single FIFO memory 40, and the motor encoder 50.

When the controller 55 receives a first encoder pulse from the motor encoder 50, the controller 55 instructs the switching network of the multiplexed photo array 308 to sequentially output the signal of each one of the photo detectors to the channel output 310. The analog processor 320 of the channel processor 315 performs analog processing on the channel output 310 in a manner similar to the analog processor 20-n in FIG. 1. The controller 55 instructs the A/D converter 325 to digitize the output of the analog processor 320. Preferably, the controller 55 coordinates the timing of the switching network of the multiplexed photo array 308 and the A/D converter 325 such that the A/D converter 325 acquires at least one digital datum from the signal of each one of the photo detectors. The A/D converter 325 writes its digital data into the memory buffer 330. Preferably, the memory buffer 330 stores the received digital data into assigned memory addresses according to their corresponding image depths. The memory buffer 330 may determine the corresponding image depths of the digital data, for example, by having the switching network of the multiplexed photo array 308 sequentially output the signals of the photo detectors in order of increasing image depth, or alternatively, in order of decreasing depth. In other words, the switching network outputs the signals of the photo detectors corresponding to shallower image depths before it outputs the signals of the photo detectors corresponding to deeper image depths.

The memory buffer 330 sequentially writes its digital data to the single FIFO memory buffer 40 via the data bus 35, preferably, in order of increasing image depth. When the controller 55 receives a second (subsequent) encoder pulse from the motor encoder 50, the digital data acquired during the first encoder pulse is outputted to the ultrasound console 12 in serial analog form in a manner similar to the electronics interface of FIG. 1. Alternatively, for the case in which the ultrasound console 12 has a digital input, the digital data may be outputted without the use of a D/A converter 45 to the ultrasound console 12 as a digital data sequence in a manner similar to the electronics interface of FIG. 2.

An advantage of the electronics interface according to this embodiment is that it reduces hardware costs by only requiring one channel processor 325 to process the output of the multiplexed photo array 308. This is because the multiplexed photo array 308 sequentially outputs the signals of its photo detectors on a single channel 310 instead of outputting the signals of its photo detectors on separate parallel channels.

Figure 4:
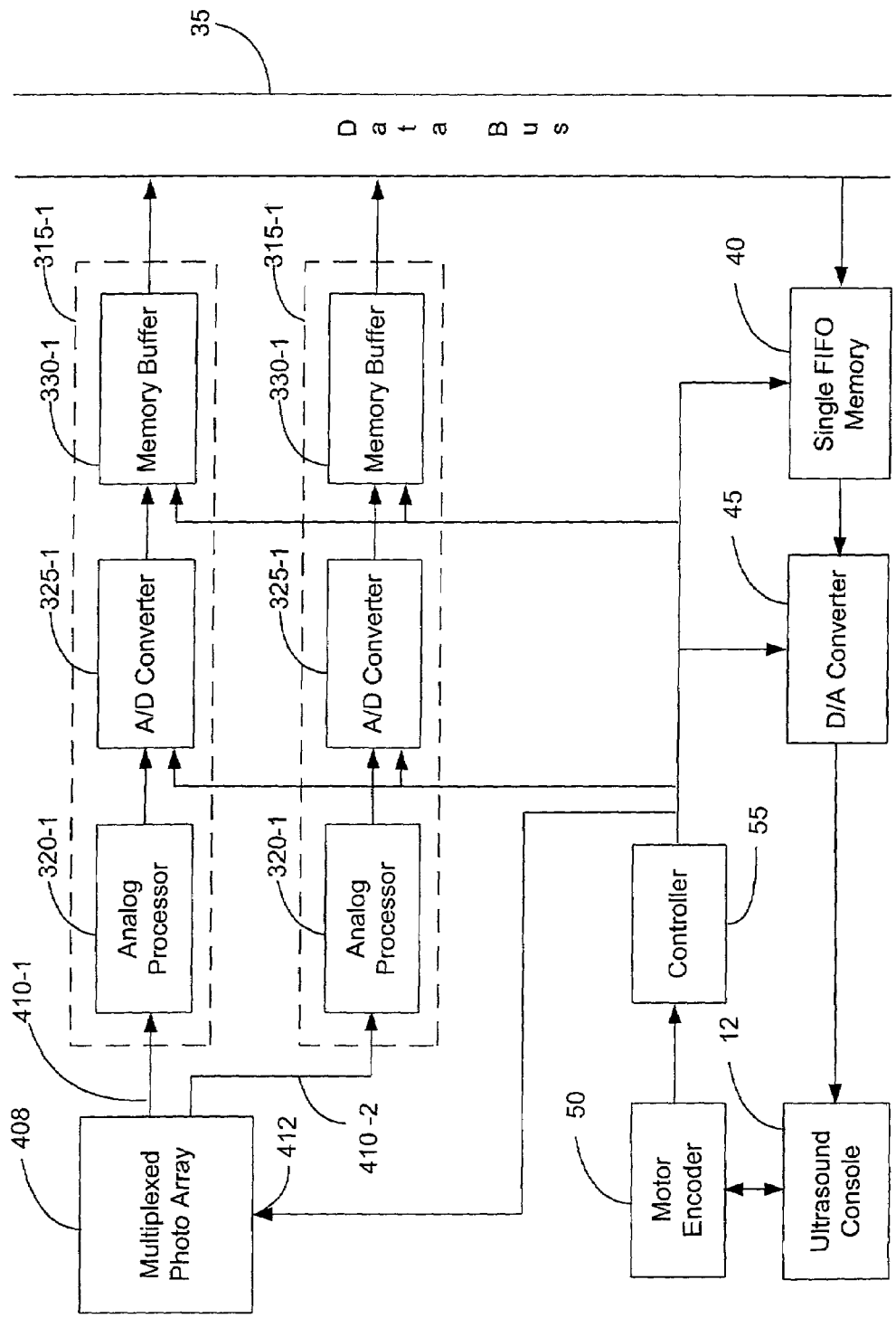
FIG. 4 is a block diagram illustrating an electronics interface coupled between a two-channel multiplexed photo array and an ultrasound console.

FIG. 4 illustrates still another embodiment of the electronics interface which is coupled to a two-channel multiplexed photo array 408. The multiplexed array 408 includes a first channel output 410-1, and a second channel output 410-2. Each one of a first half of the photo detectors of the multiplexed photo array 408 can be dynamically coupled to the first channel output 410-1 via a first switching network (not shown). Each one of a second half of the photo detectors can be dynamically coupled to the second channel 410-2 via a second switching network (not shown).

The electronics interface of FIG. 4 includes a first and second channel processor 315-1, 315-2 coupled to the first and second channel output 410-1, 410-2, respectively. Each channel processor 315-1, 315-2 includes an analog processor 320-1, 320-2, an A/D converter 325-1, 325-2 and a memory buffer 330-1, 330-2. The output of the memory buffer 330-1, 330-2 of each one of the channel processors 315-1, 315-2 is coupled to the data bus 35. Alternatively, the first and second channel processors 315-1, 315-2 may share a common memory buffer. In this alternative case, the output of the A/D converter 325-1, 325-2 of each one of the channel processors 315-1, 315-2 would be coupled to the common memory buffer.

When the controller 55 receives a first encoder pulse from the motor encoder 50, the controller 55 instructs the first switching network of the multiplexed photo array 408 to sequentially output the signal of each one of the first half of the photo detectors to the first channel output 410-1. Similarly, the controller 55 instructs the second switching network to sequentially output the signal of each one of the second half of the photo detectors to the second channel output 410-2. The analog processor 320-1, 320-2 of each one of the channel processors 315-1, 315-2 performs analog processing on the respective channel output 410-1, 410-2. The controller 55 instructs each A/D converter 325-1, 325-2 to digitize the output of the respective analog processor 320-1, 320-2. Preferably, the controller 55 coordinates the timing of the first switching network and the A/D converter 325-1 of the first channel processor 315-1 such that the A/D converter 325-1 acquires at least one digital datum from the signal of each one of the first half of the photo detectors. Similarly, the controller 55 coordinates the timing of the second switching network and the A/D converter 325-2 of the second channel processor 315-2 such that the A/D converter 352-2 acquires at least one digital datum from the signals of each one of the second half of the photo detectors. Each one of the A/D converters 325-1, 325-2 writes its digital data into the respective memory buffer 330-1, 330-2. Preferably, each memory buffer 330-1, 330-2 stores its received digital data into assigned memory spaces according to their corresponding image depth.

The memory buffers 330-1, 330-2 sequentially write their digital data to the single FIFO memory buffer 40 via the data bus 35, preferably, in order of increasing image depth. When the controller 55 receives a second (subsequent) encoder pulse from the motor encoder 50, the digital data acquired during the first encoder pulse is outputted to the ultrasound console 12 in serial analog form in a manner similar to the electronics interface of FIG. 1. Alternatively, for the case in which the ultrasound console has a digital input, the digital data may be outputted to the ultrasound console 12 as a digital data sequence in a manner similar to the electronics interface of FIG. 2.

An advantage of the electronics interface according to this embodiment is that it this may achieve higher data read out rates compared with the electronics interface of FIG. 3. This is because the electronics interface according to this embodiment uses two channel processors to simultaneously process two separate outputs of the multiplexed photo array. Thus, while adding to the hardware cost of the electronics interface, additional channel processors may increase the data read out rate of the electronics interface. Those skilled in the art will appreciate that the multiplexed photo array and the electronics interface may include any number of channels.

It is contemplated that any embodiment described in this patent specification can be modified such that, for example, the number of any of the components can be increased or decreased as desired. Further, it is contemplated that features shown in one embodiment may be added to those of another embodiment, or features shown in one embodiment may be deleted, as desired. Also, the output of the electronics interface of any embodiment may be either digital, analog, or any other format required by the ultrasound console.

While various embodiments of the application have been described, it will be apparent to those of ordinary skill in the art that many embodiments and implementations are possible that are within the scope of the invention. Therefore, the invention is not to be restricted or limited except in accordance with the following claims and their equivalents.

What is claimed is:

1. An electronics interface for interfacing a multiplexed photo array comprising at least one channel output with an ultrasound console, each one of the channel outputs capable of outputting a signal from each one of a plurality of photo detectors, each one of the plurality of photo detectors corresponding to a different image depth, the electronics interface comprising:
   at least one channel processor, each one of the channel processors having an input coupled to one of the channel outputs of the multiplexed photo array and an output, wherein each one of the channel processors acguires digital data from the respective channel output;
   a data bus coupled to the output of each one of the channel processors;
   a memory buffer having an input coupled to the data bus and an output; and
   a digital-to-analog converter having an input coupled to the output of the memory buffer and an output, wherein the output of the digital-to-analog converter is coupled to the ultrasound console.

2. The electronics interface of claim 1, wherein the multiplexed photo array comprises exactly one channel output.

3. The electronics interface of claim 1, wherein the multiplexed photo array comprises exactly two channel outputs.

4. The An electronics interface for interfacing a multiplexed photo array comprising at least one channel output with an ultrasound console, each one of the channel outputs capable of outputting a signal from each one of a plurality of photo detectors, each one of the plurality of photo detectors corresponding to a different image depth, the electronics interface comprising:
   at least one channel processor, each one of the channel processors having an input coupled to one of the channel outputs of the multiplexed photo array and an output, wherein each one of the channel processors acguires digital data from the respective channel output;
   a data bus coupled to the output of each one of the channel processors;
   a memory buffer having an input coupled to the data bus and an output; and
   a controller coupled to an ultrasound motor encoder for synchronizing the electronics interface and the multiplexed photo array with the ultrasound console.

5. The electronics interface of claim 4, the controller instructs each one of the channel outputs of the multiplexed photo array to sequentially output the signal from each one of its respective plurality of photo detectors when the controller receives an encoder pulse from the ultrasound motor encoder.

6. The electronics interface of claim 5, wherein the controller coordinates the timing of the channel outputs of the photo array and the channel processors such that each one of the channel processors acquires at least one digital datum for each photo detector signal outputted by the respective channel output.

7. The electronics interface of claim 6, wherein each one of the channel processors writes its digital data into the memory buffer via the data bus.

8. The electronics interface of claim 7, further comprising a digital-to-analog converter having an input coupled to the output of the memory buffer and an output coupled to the ultrasound console.

9. The electronics interface of claim 8, wherein the controller instructs the memory buffer to output the digital data received from the channel processors to the digital-to-analog converter when the controller receives a subsequent encoder pulse from the ultrasound motor encoder.

10. The electronics interface of claim 9, wherein the memory buffer outputs the digital data to the digital-to-analog converter in the form of a digital data sequence.

11. The electronics interface of claim 10, wherein the digital data in the digital data sequence are arranged in order of increasing image depth.

12. The electronics interface of claim 10, wherein the digital-to-analog converter converts the received digital data into an analog signal and outputs the analog signal to the ultrasound console.

13. The electronics interface of claim 12, wherein the digital-to-analog converter outputs the analog signal to the ultrasound console in the form of a serial analog signal.

14. The electronics interface of claim 7, further comprising a logic control having an input coupled to the memory buffer and an output coupled to a digital input of the ultrasound console.

15. The electronics interface of claim 14, wherein the controller instructs the logic control to transfer the digital data stored in the memory buffer to the ultrasound console when the controller receives a subsequent encoder pulse from the ultrasound motor encoder.

16. The electronics interface of claim 15, wherein the control logic transfers the digital data to the ultrasound console in form of a digital data sequence.

17. The electronics interface of claim 16, wherein the digital data in the digital data sequence are arranged in order of increasing image depth.

* * * * *